(12) United States Patent
Sildve et al.

(10) Patent No.: US 7,762,810 B2
(45) Date of Patent: Jul. 27, 2010

(54) APPARATUS AND METHOD FOR POSITIONING DENTAL ARCH TO DENTAL ARTICULATOR

(75) Inventors: Peter O. Sildve, Glen Ellyn, IL (US); Edward Dschida, Woodstock, IL (US)

(73) Assignee: B. F. Wehmer Co., Inc., Lombard, IL (US)

( * ) Notice: Subject to any disclaimer, the term of this patent is extended or adjusted under 35 U.S.C. 154(b) by 546 days.

(21) Appl. No.: 11/741,464

(22) Filed: Apr. 27, 2007

(65) Prior Publication Data

US 2007/0224573 A1     Sep. 27, 2007

Related U.S. Application Data

(62) Division of application No. 10/681,620, filed on Oct. 8, 2003, now abandoned.

(60) Provisional application No. 60/417,600, filed on Oct. 9, 2002.

(51) Int. Cl.
*A61C 11/00* (2006.01)
(52) U.S. Cl. ......................................................... 433/56
(58) Field of Classification Search ................. 433/213, 433/54–67
See application file for complete search history.

(56) References Cited

U.S. PATENT DOCUMENTS

| | | | |
|---|---|---|---|
| 1,052,806 A | 2/1914 | Evans | |
| 2,225,274 A | 12/1940 | MacGoun | |
| 2,334,643 A | 11/1943 | Moore | |
| 2,613,440 A | 10/1952 | Murray et al. | |
| 2,621,406 A | 12/1952 | McPhee | |
| 2,748,481 A | 6/1956 | Glueck | |
| 2,772,477 A | 12/1956 | Miller | |
| 2,959,857 A | 11/1960 | Stoll | |
| 3,200,497 A | 8/1965 | Goodfriend | |
| 3,218,716 A | 11/1965 | Stuart | |
| 3,336,670 A | 8/1967 | Heydenreich | |
| 3,854,208 A | 12/1974 | Arant | |
| 4,330,277 A | 5/1982 | Beu | |

(Continued)

OTHER PUBLICATIONS

Dawson, Peter E., "Evaluation, Diagnosis and Treatment of Occlusal Problems", second edition, St. Louis, MO, The C.V. Mosby Co., 1989, p. 29.

(Continued)

*Primary Examiner*—Cris L Rodriguez
*Assistant Examiner*—Matthew M Nelson
(74) *Attorney, Agent, or Firm*—Ice Miller LLP

(57) ABSTRACT

A positioning apparatus and method for using the positioning apparatus to position a dental arch model in a dental articulator, simulating the position of dental arch in a skull. The positioning apparatus includes a first member, a second member that slides with respect to the first member, and a third member that slides with respect to the second member. A locating member on the second member and one or more adjustment members on the third member impart an orientation to a mounting surface representative of a plane in which a dental arch lies. A maxillary tray having radio-opaque members may be mounted to the mounting surface. X-ray data obtained while the maxillary tray is engaged with a patient's teeth is used to determine the position and orientation of a dental arch model while said model is engaged with the maxillary tray on the mounting surface.

20 Claims, 10 Drawing Sheets

U.S. PATENT DOCUMENTS

| | | |
|---|---|---|
| 4,391,589 A | 7/1983 | Monfredo et al. |
| 4,501,556 A | 2/1985 | Zelnigher |
| 4,609,351 A | 9/1986 | Blair |
| 4,624,639 A | 11/1986 | Wong |
| 4,634,377 A * | 1/1987 | Behrend ..................... 433/73 |
| 4,892,480 A | 1/1990 | Levandoski |
| 5,090,901 A | 2/1992 | Levandoski |
| 5,160,262 A | 11/1992 | Alpern et al. |
| 5,176,515 A | 1/1993 | Andrews |
| 5,320,526 A | 6/1994 | Tuneberg |
| 5,320,528 A | 6/1994 | Alpern et al. |
| 5,338,198 A | 8/1994 | Wu et al. |
| 5,416,822 A | 5/1995 | Kunik |
| 5,725,376 A | 3/1998 | Poirier |
| 5,738,515 A | 4/1998 | Leever |
| 6,152,731 A | 11/2000 | Jordan et al. |
| 6,152,732 A | 11/2000 | Lindekugel |
| 2002/0177104 A1 | 11/2002 | Klein et al. |

OTHER PUBLICATIONS

McMinn, R.M.H., "Color Atlas of Head and Neck Anatomy", Chicago, IL, Year Book Medical Publishers, Inc., 1981, pp. 10-23.

Jacobson, Alexander, "Radiographic Cephalometry: From Basics Videoimaging", Carol Stream, IL, Quintessence Publishing Co., Inc., 1995, pp. 276-303.

Thurow, Raymond C., "Edgewise Orthodontics", St. Louis, MO, The C.V. Mosby Co., 1966, pp. 261-262.

Dentaart, Inc., "AART™ Anatomic Accurate Reproducible Transfer Technique Manual", Manual, Sep. 1999, 32 pgs., DENTAART, Inc., Tampa, FL.

Mark L. Pitel, DMD, "Clinical Management of a Work Dentition with a New Polycentric Occlusal System", Article, Aug. 2000, Denistry Today, pp. 1-6.

GAC International, "Articulator AMTECH MG1", Brochure, 4 pages. GAC International, Central Islip, NY.

* cited by examiner

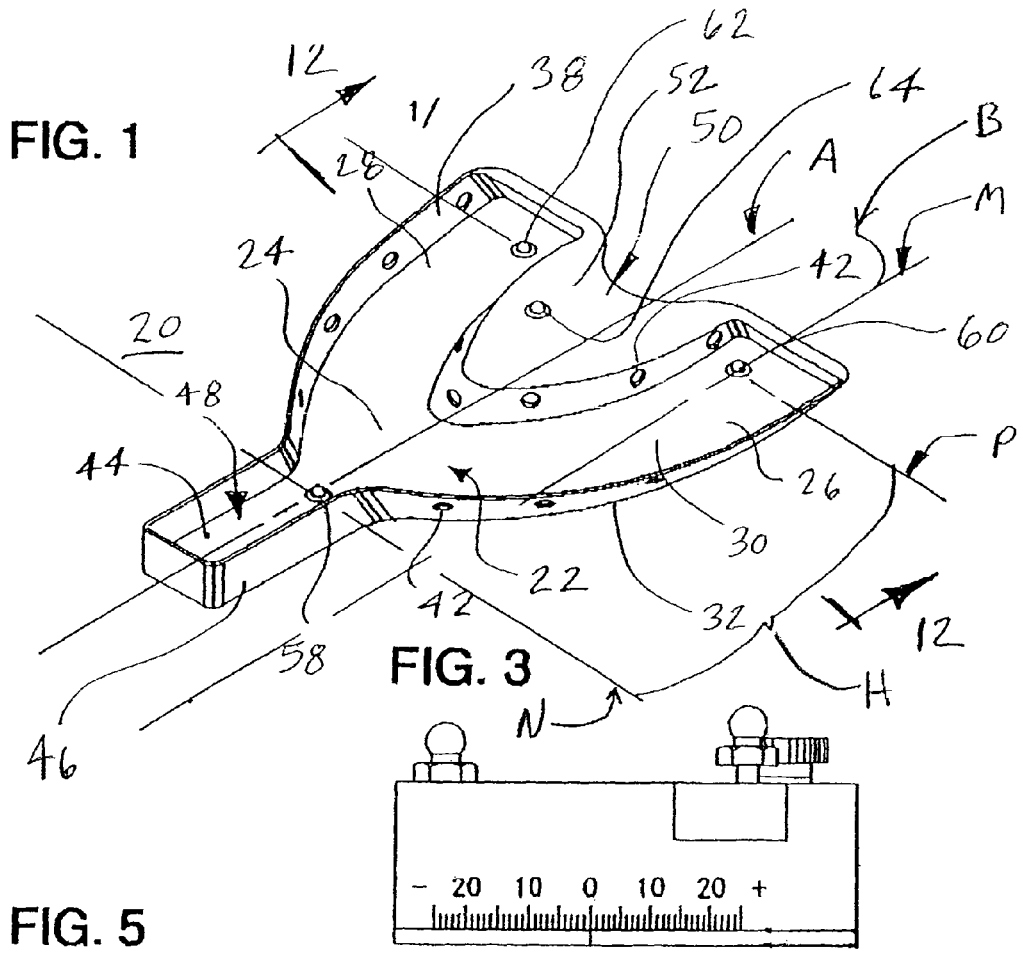
FIG. 1
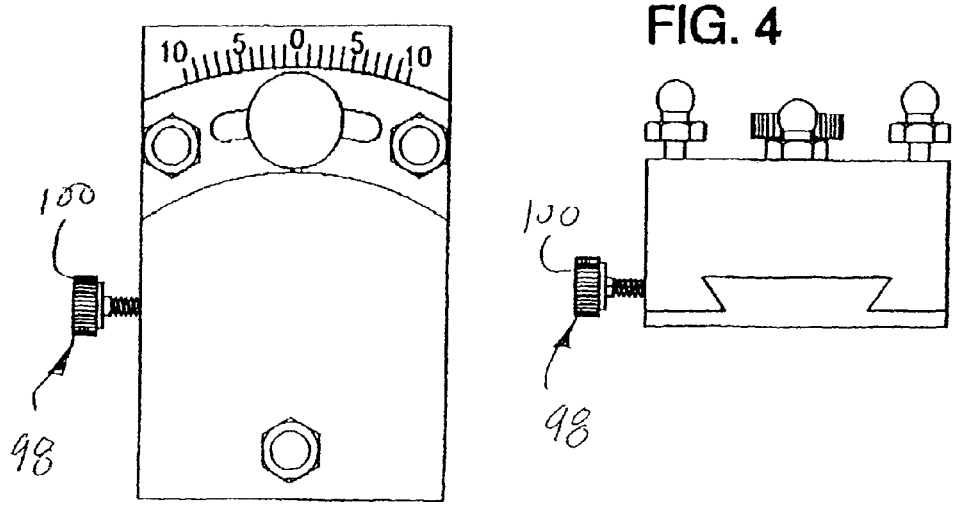
FIG. 3
FIG. 5
FIG. 4

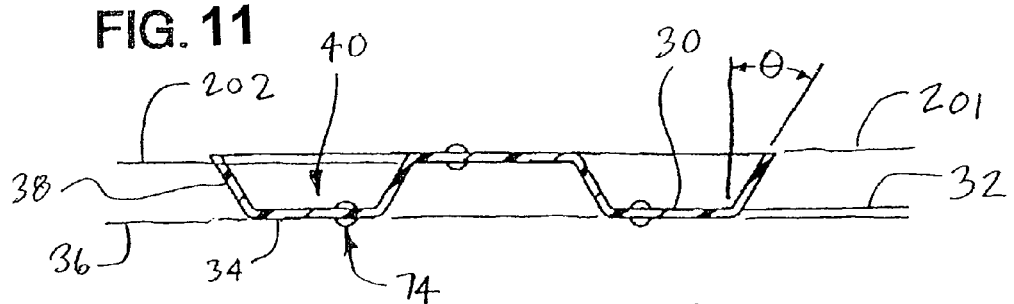
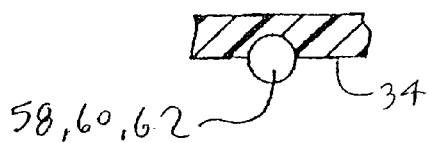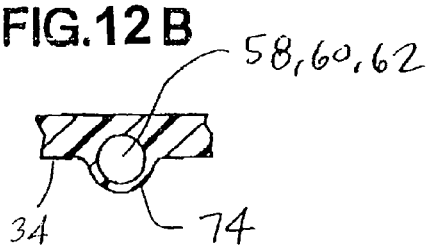
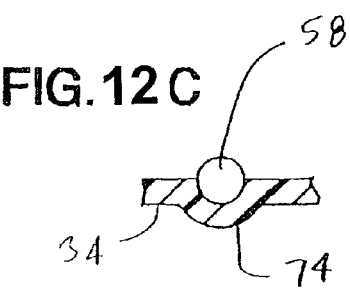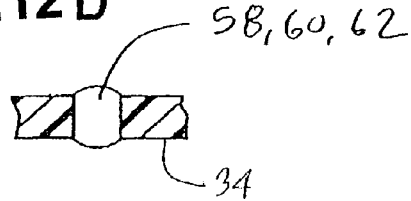
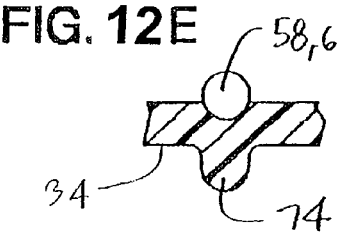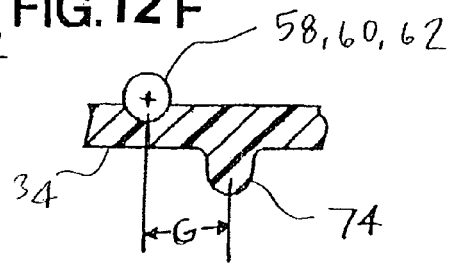
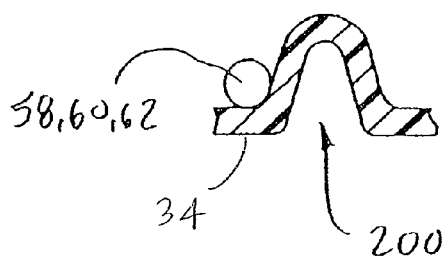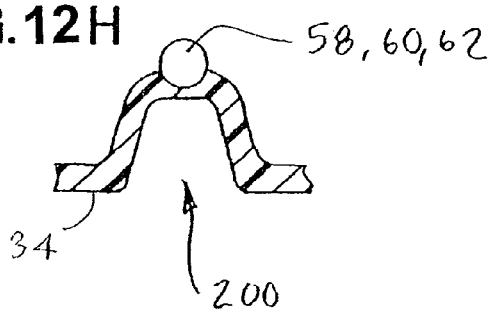

APPARATUS AND METHOD FOR POSITIONING DENTAL ARCH TO DENTAL ARTICULATOR

CROSS REFERENCE TO RELATED APPLICATION

This application is a divisional of prior application Ser. No. 10/681,620, filed Oct. 8, 2003, which claims the priority from U.S. Provisional Application No. 60/417,600 filed Oct. 9, 2002.

FIELD OF THE INVENTION

The present invention relates to dental articulators and more particularly to apparatuses and methods for positioning and securing a model of a dental arch within a dental articulator.

BRIEF DESCRIPTION OF THE DRAWINGS

In the drawings illustrating embodiments of the present invention:

FIG. 1 is a perspective view of the maxillary matrix tray of the present invention;

FIG. 3 is a side view of the positioning apparatus of FIG. 2;

FIG. 4 is an end view of the positioning apparatus of FIG. 2;

FIG. 5 is a top view of the positioning apparatus of FIG. 2;

FIG. 11 is a cutaway edge view of the maxillary matrix tray of FIG. 1;

FIGS. 12A-12H are partial cutaway views of the maxillary matrix tray of FIG. 1 showing various embodiments for securing a radio-opaque member to the tray;

DETAILED DESCRIPTION OF THE INVENTION

Figure 2:
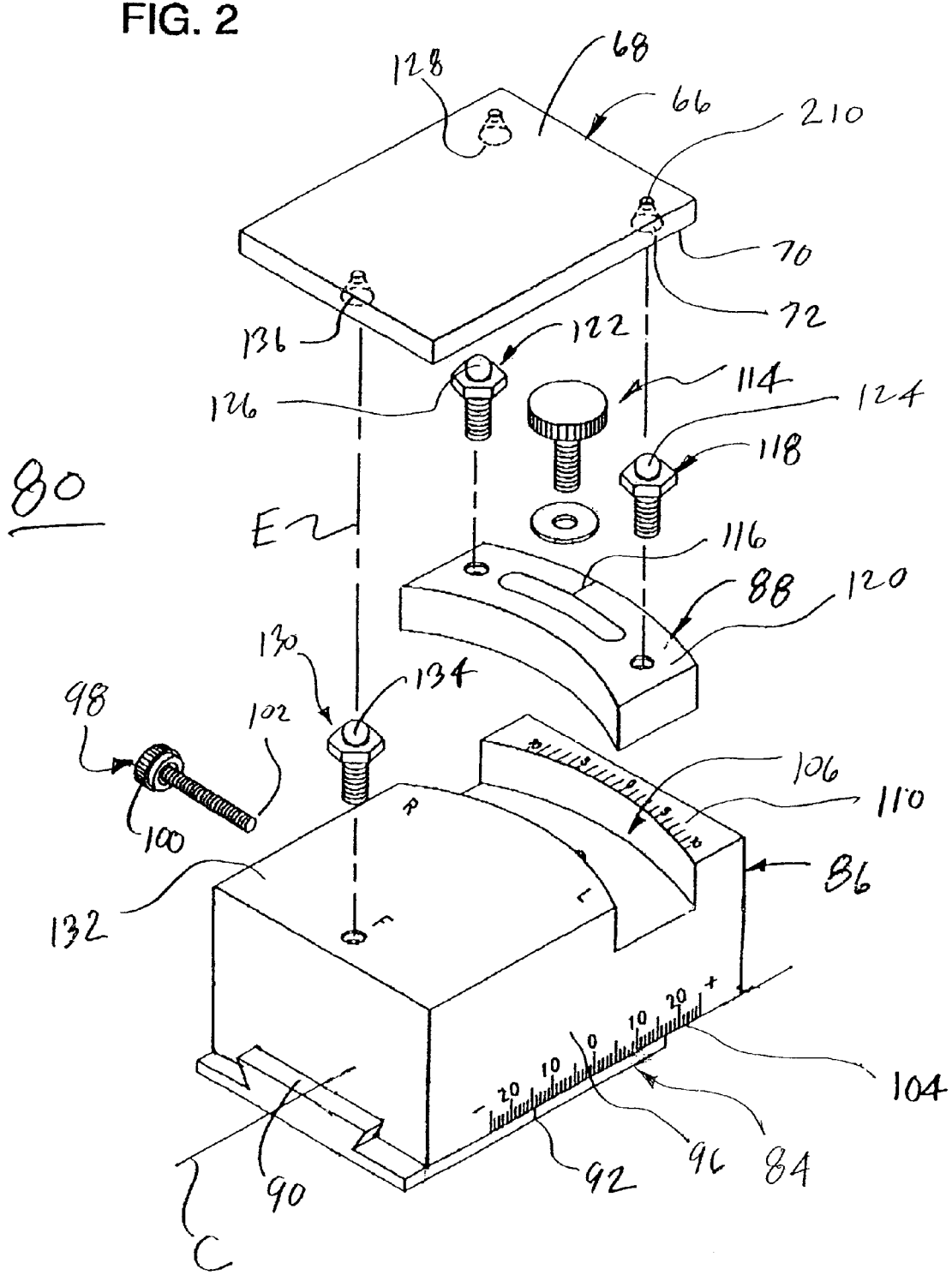
FIG. 2 is an exploded perspective view of the positioning apparatus of the present invention.

FIGS. 1 and 11 show a maxillary matrix tray 20 for receiving an impression of an upper dental arch. Maxillary matrix tray 20 generally comprises a base 22 having an axis of symmetry A. Base 22 defines a generally U-shaped portion 24 for receiving a dental arch of a patient. U-shaped portion 24 includes two spaced-apart wing portions 26, 28. Base 22 also has a first face 30 defining a first plane 32 and a second face 34 opposite first face 30 defining a second plane 36. Base 22 may be formed from a plastic material.

As seen in FIGS. 1 and 11, a wall 38 extends from an edge of base 22 at an angle with respect to first plane 32 of base 22, base 22 and wall 38 combining to form a receptacle, generally designated 40. A plurality of generally evenly-spaced holes 42 may be formed along wall 38.

In one embodiment, a tongue portion 44 projects from base 22 opposite a junction of wing portions 26, 28. Tongue portion 44 is generally planar and may include a wall 46 extending from an edge thereof with respect to a plane defined by an extension of first face 30. Tongue portion 44 and wall 46 combine to form a second receptacle 48 contiguous with receptacle 40 formed by base 22 and wall 38 extending from base 22. The structure defined by tongue portion 44 and wall 46 is used to grip and manipulate maxillary matrix tray 20 without the need to grasp the portion of the apparatus that is inserted into the mouth of a patient.

Maxillary matrix tray 20 may also include an extension, generally designated 50, projecting from U-shaped portion 24. Extension 50 may include a portion 52 connecting spaced-apart wing portions 26, 28 and having a first face 54 defining a first plane 201 and a second face 56 opposite first face 54 defining a second plane 202. Extension 50 may be formed integral with base 22 and may also be formed from a plastic material.

Referring to FIG. 1, three radio-opaque members 58, 60, 62 are secured to base 22. At least two of the radio-opaque members (for example 58 and 60) are spaced apart at a pre-determined distance from one another. In one embodiment, the position of radio-opaque member 60 with respect to radio-opaque member 58 is determined by specifying an axis M extending through wing portion 26 parallel to axis of symmetry A and spaced apart a first pre-determined distance B from axis A. Another axis N is then specified extending through radio-opaque member 58 perpendicular to axis A. A third axis P is also specified which is both perpendicular to axis A and spaced apart a second predetermined distance H from axis N. The location of radio-opaque member 60 is then determined by the intersection of axes N and P. In the embodiment shown, first pre-determined distance B is equal to approximately 20 mm and pre-determined distance H is approximately 50 mm.

Radio-opaque members 58, 60, 62 may be formed from a metallic substance or from any substance sufficiently resistant to penetration by X-rays so as to be clearly visible on an exposed diagnostic X-ray film. Radio-opaque members 58, 60, 62 may be spherical or may be formed in any one of a variety of shapes according to space constraints and/or diagnostic process requirements.

Referring to FIG. 1, in one embodiment of the invention, a first radio-opaque member 58 is secured to and positioned on base 22 approximately along axis of symmetry A, and a second radio-opaque member 60 is secured to and positioned within a first wing portion 26 and spaced apart from axis of symmetry A. A third radio-opaque member 62 may be positioned in a second wing portion 28 and spaced apart from axis of symmetry A on an opposite side of axis A from radio-opaque member 60. In addition, second radio-opaque member 60 and third radio-opaque member 62 may be spaced a substantially equal distance from axis of symmetry A. Second radio-opaque member 60 and third radio-opaque member 62 may also be spaced a substantially equal distance from first radio-opaque member 58.

Radio-opaque members 58, 60, 62 may be secured to base 22 along either first face 30 or second face 34 using any one of a variety of methods. For example, if base 22 is formed from a plastic material, the radio-opaque members may be molded or press-fit into base 22. Radio-opaque members 58, 60, 62 may alternatively be secured to base 22 using an adhesive.

If base 22 includes an extension 50, another radio-opaque member 64 may also be secured to extension connecting portion 52. Radio-opaque member 64 secured to extension connecting portion 52 is generally positioned closer to one of wing portions 26, 28 than to the remaining wing portion. Radio-opaque member 64 may be secured to connecting portion 52 along either first face 54 or second face 56 of connecting portion 52 using any one of a variety of methods. For example, if connecting portion 52 is formed from a plastic material, radio-opaque member 64 may be molded or press-fit into connecting portion 52. Alternatively, radio-opaque member 64 may be secured to connecting portion 52 using an adhesive.

The maxillary matrix tray of the present invention also includes means for securing the tray to a mounting surface of a mounting member. FIG. 2 shows an example of a mounting member 66 on which maxillary matrix tray 20 may be mounted for diagnostic purposes in a manner to be discussed in detail later. In this embodiment, mounting member 66 comprises a flat plate having a mounting surface 68 and a positioning surface 70 opposite mounting surface 66. Mounting surface 68 includes at least one cavity 210 formed for receiving therein a complementary projection extending from maxillary matrix tray 20, and positioning surface 70 includes at least one cavity 72 for receiving therein a portion of a mounting surface adjustment member 118, in a manner to be described in detail later.

Referring to FIG. 11, the means for securing maxillary matrix tray 20 to mounting surface 68 shown in FIG. 2 comprises a projection, generally designated 74, extending from second plane 36 defined by second face 34 of base 22. Projection 74 may be a feature formed integral with base 22. Alternatively, projection 74 may be formed a separate feature attached to base 22 after the base is formed.

FIGS. 11 and 12A-12H show examples of how projection 74 may be formed in maxillary matrix tray 20 and examples of possible relationships between one of radio-opaque members 58, 60, 62 and projection 74. In the examples that follow, projection 74 represents any one of several possible projections extending from pre-determined locations along second plane 36 for insertion into corresponding cavities in mounting surface 68.

As seen in FIG. 12F, projection 74 may be offset from one of radio-opaque members 58, 60, 62 by a pre-determined distance G. As seen in FIG. 12E, projection 74 may alternatively be positioned opposite one of radio-opaque members 58, 60, 62 such that the location of projection 74 corresponds to the location of one of radio-opaque members 58, 60, 62, and vice versa.

In addition, as seen in FIGS. 12A-D, projection 74 may be formed in any one of a variety of ways by one of the radio-opaque members secured to the base. For example, as seen in FIGS. 12B and 12C, a radio-opaque member 58, 60, 62 may be molded or press fit into base 22 forming a nodule 74 extending from second plane 36 of base 22. Referring to FIGS. 12A and 12D, one of radio-opaque members 58, 60, 62 may alternatively be secured to base 22 so as to project from second plane 36.

In an alternative embodiment shown in FIGS. 12G-H, maxillary matrix tray 20 may include a cavity 200 formed along second face 34 for receiving therein a complimentary projection extending from mounting surface 68. As seen in FIG. 12G, cavity 200 may be offset from one of radio-opaque members 58, 60, 62 by a pre-determined amount. Alternatively, as seen in FIG. 12H, cavity 200 may be positioned opposite one of radio-opaque members 58, 60, 62 such that the location of cavity 200 corresponds to the location of one of radio-opaque members 58, 60, 62, and vice versa.

A positioning apparatus for use in positioning a model of a dental arch will now be described with reference to FIGS. 2 and 4-6.

FIG. 2 shows a positioning apparatus, generally designated 80, for use in positioning a model of a dental arch (not shown) within a dental articulator to simulate the position of the dental arch in a skull. In a first embodiment, positioning apparatus 80 includes a first member 84, a second member 86 operatively associated with first member 84, and a third member 88 operatively associated with second member 86. As seen in FIG. 2, in one embodiment, first member 84, second member 86 and third member 88 are each formed from metal plates. The metal plates comprising first member 84, second member 86 and third member 88 are suitably machined and finished such that they interlock and may slide easily with respect to each other when in contact with each other.

As stated above, second member 86 is slidingly mounted on first member 84 and is positionable with respect to first member 84 along first axis C. Referring to FIG. 2, a dovetail-shaped tongue 90 formed in first member 84 is slidingly received within a correspondingly shaped groove formed in second member 86, simultaneously securing second member 86 to first member 84 and enabling second member 86 to slide with respect to first member 84 along axis C. A reference indicator mark 92 is formed on a surface of first member 84. A series of coordinate indicator marks 104 is provided along an edge of second member 86 adjacent indicator mark 92 of first member 84. Second member 86 may be positioned with respect to first member 84 in correspondence with a pre-determined set of coordinate values by aligning reference indicator mark 92 with a corresponding one of coordinate indicator marks 104, in a manner to be described in detail later.

Referring to FIGS. 2 and 5, a locking member may be provided to lock first member 84 and second member 86 in a desired relationship. In one embodiment, the locking member is shown in the form of a set screw 98 mounted in a tapped through hole (not shown) which extends through second member 86 to first member 84. Screw 98 includes a knob 100 for grasping by a user. When first member 84 and second member 86 are positioned in the desired relationship, knob 100 is turned by a user to advance screw 98 into the tapped hole until an end 102 of screw 98 presses against first member 84, securing second member 86 with respect to first member 84. In the embodiment shown, locking member screw 98 is attached to second member 86. Alternatively, locking member screw 98 may be attached to first member 82. Referring to FIG. 2, second member 86 may include an arcuate slot 106 for receiving third member 88 in a sliding relationship therein. Third member 88 has a generally arcuate configuration and is slidingly received within arcuate slot 106 on second member 86. As the arc formed by slot 106 is centered about second axis E, when sliding within slot 106 third member 86 is positionable about second axis E, which is generally perpendicular to first axis C. A locking member in the form of a set screw 114 may be used to secure third member 88 in a pre-determined relationship with respect to second member 86. In the embodiment shown, locking member screw 114 is attached to third member 88. Alternatively, locking member screw 114 may be attached to second member 86. In addition, it is understood that other suitable means may be employed to secure the various members of the positioning apparatus in position with respect to each other. A reference mark 116 is provided along a surface of third member 88 and a series of coordinate indicator marks 110 is provided along an edge of second member 86 adjacent indicator mark 116 of third member 88. Third member 88 may be positioned with respect to second member 86 in correspondence with a pre-determined set of coordinate values by aligning reference indicator mark 116 with a corresponding one of coordinate indicator marks 110, in a manner to be described in detail later.

In addition, at least one adjustment member 118, is provided which is operatively associated with third member 88 and is adjustably positionable with respect to a surface 120 of third member 88. Adjustment member 118 controls the tilt of mounting member 66 with respect to surface 120 of third member 88. In the embodiment shown, two adjustment members 118, 122 are provided in the form of screws extending from a surface of third member 88. In addition to the method shown for adjusting the tilt of mounting member 66, the present invention contemplates the use of any one of several known methods for providing one or more adjustable bearing surfaces projecting above surface 120 and configured for receiving a portion of mounting member 66 thereon. Adjustment member screws 118, 122 have rounded uppermost surfaces 124, 126, respectively, for insertion into complimentary cavities 72, 128 in mounting member 66, for positioning and securing mounting member 66 on adjustment member screws 118, 122.

Referring to FIG. 2, a locating member may be positioned along second axis E in operative association with second member 86 to more precisely position a forward portion of mounting member 66 along axis E, so as to facilitate rotation of mounting member 66 about axis E. In one embodiment, locating member comprises a screw 130 extending from a hole in surface 132 of second member 86 and rotatable about third axis E to adjust a height above surface 132 which screw 130 projects. In the embodiment shown, surface 120 of third member 88 is substantially flush with surface 132 of second member 86. Locating member screw 130 has a rounded uppermost surface 134 for insertion into a complimentary cavity 136 in mounting member 66, in a manner to be described in detail later.

As seen in FIG. 2, the hole from which locating member 130 projects is labeled "F" (for "front"). Similarly, holes from which adjustment members 118, 122 project are labeled "R" (for "patient's right") and "L" (for "patient's left"), respectively. These labels are used to properly orient a model of the dental arch positioned upon mounting member 66, in a manner to be described in detail later.

Mounting member 66 is operatively associated with locating member 130 and adjustment members 118, 122 and adapted to receive maxillary matrix tray 20 thereon. In the presently described embodiment, mounting member 66 is associated with locating member 130 and adjustment members 118, 122 by means of a series of cavities 72, 128, 136 formed in positioning surface 70 of mounting member 66 adapted to receive rounded head portions of locating member 130 and adjustment members 118, 122 therein such that mounting member 66 will rest atop and be positionally secured to the rounded head portions of locating member 130 and adjustment members 118,122.

In the present invention, mounting member surface 68 is designed to simulate the position and orientation of the maxillary occlusal plane of a given patient. By varying the amount by which locating member screw 130 projects above second member surface 132 and by varying the amounts by which adjustment member screws 118, 122 project above third member surface 120 according to a pre-determined set of coordinate values, a desired orientation may be imparted to mounting surface 68 and, thus, to a model of a dental arch mounted on mounting surface 68.

A method for orienting mounting member surface 68 so as to simulate the orientation of the maxillary occlusal plane of a dental patient will now be discussed.

To orient mounting surface 68 in the desired manner, each component of positioning apparatus 80 described above is positioned with respect to another component according to a set of coordinate values. These coordinate values represent the orientation of the maxillary occlusal plane of an individual patient and are therefore derived for each individual patient using measurements of portions of the patient's head in combination with interpretation of anterior (frontal), lateral (side) and submental vertex X-ray views of the patient's head with the patient having their teeth engaged in the maxillary matrix tray 20 discussed above. Measurements from the resulting x-rays portraying the radio opaque members are made with accommodations to the measurements based on the projection of the x-rays from the patient's head to the x-ray plate. When the components of positioning apparatus 80 are positioned according to the coordinate values, the orientation of mounting surface 68 will correspond to the orientation of the maxillary occlusal plane of the patient.

Referring to FIG. 2, in a first step, the position of second member 86 with respect to first member 84 is adjusted along axis C such that a pre-determined one of second member indicator marks 104 is aligned with reference mark 94 located on first member 84 so as to correspond to a first coordinate of the set of coordinates. After second member 86 has been positioned in the desired position, second member 86 may be locked in this position using locking member screw 98.

Next, the position of third member 88 with respect to second member 86 is adjusted within arcuate slot 106 such that a predetermined one of second member indicator marks 110 is aligned with reference mark 116 located on third member 88 so as to correspond to a second coordinate of the set of coordinates. After third member 88 has been positioned in the desired position, third member 88 may be locked in this position using locking member screw 114.

In the next series of steps, the amounts by which adjustment member screws 118, 122 and locating member screw 130 project above surfaces 120 and 132, respectively, are adjusted by rotation of the screws in the appropriate direction. A counterclockwise rotation of the screws will increase the distance above surfaces 120, 132 which screws 118, 122 and 130 project, while a clockwise rotation will decrease the amount by which the screws project above surfaces 120 and 132.

Figure 6:
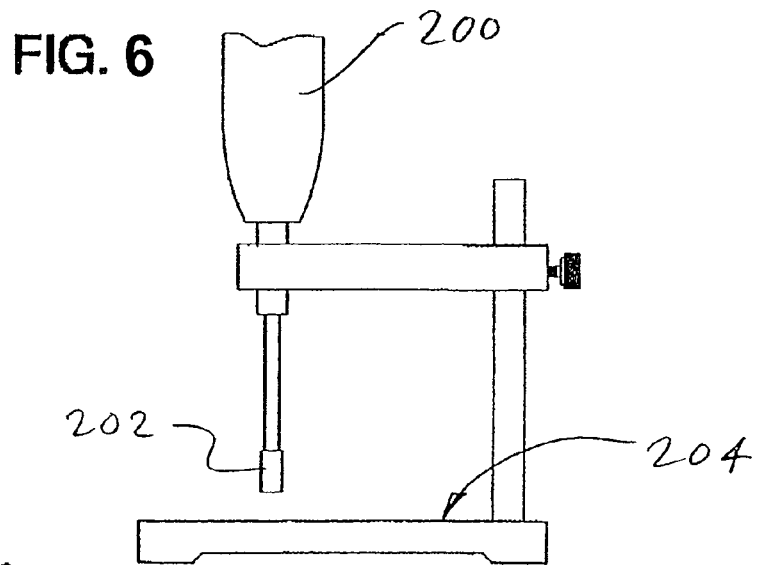
FIG. 6 is a side view of an indicator mechanism for measuring positional differences between portions of the apparatus of FIG. 2.

FIGS. 6-10 illustrate a representative example of how adjustment member screws 118, 122 and locating member screw 130 may be positioned corresponding to respective coordinate values of the set of coordinates. FIG. 6 shows an indicator 200 adapted to measure a linear displacement of a portion of a probe 202 incorporated into the indicator. Indicator 200 is suspended above a mounting surface 204 on which positioning apparatus 80 is to be placed for measuring the heights above a pre-determined reference surface, or surfaces, which rounded-head portion 134 of locating member 130 and rounded-head portions 124, 126 of adjustment members 122, 118 project. Referring to FIG. 2, in the present embodiment the reference surface comprises surface 132 of second member 86, and the height of locating member 130 is measured with respect to surface 132 of second member 86.

However, the height of locating member 130 may be measured with respect to another, alternative reference surface provided the method used to generate the coordinate values is adapted to account for the difference in vertical distance between surface 132 of second member 86 and the alternative reference surface.

Figure 7:
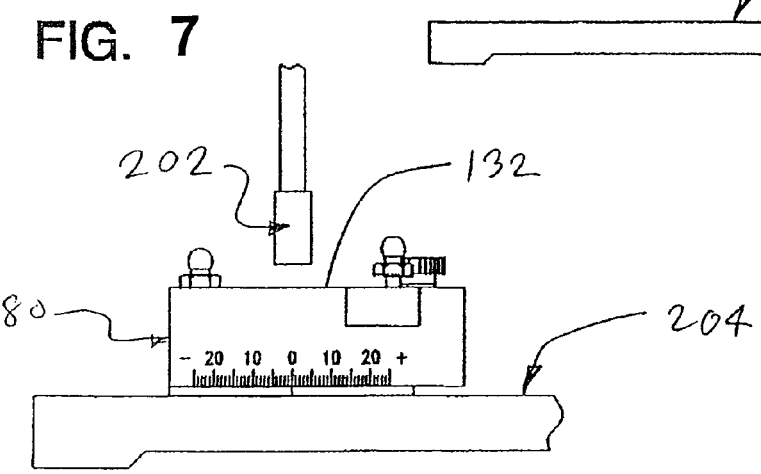
FIGS. 7-10 are side views of the positioning apparatus of FIG. 2 mounted on the indicator mechanism of FIG. 6.
Figure 8:
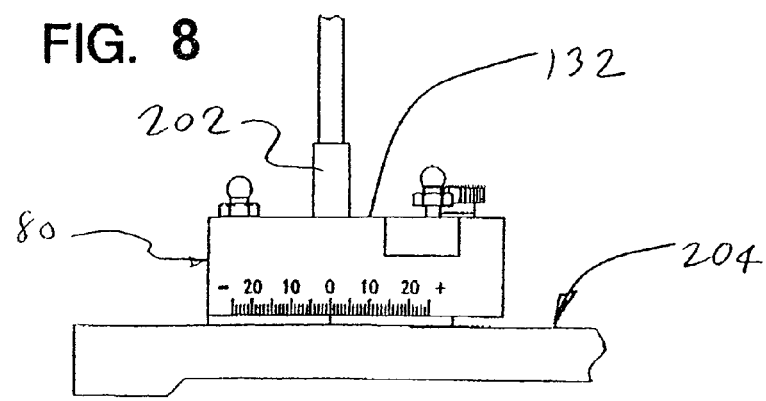

Referring to FIGS. 2 and 7, locating member 130 is first positioned with respect to surface 132 so as to minimize the height above surface 132 which member 130 projects. In the embodiment shown, a flange of locating member screw 130 is in contact with surface 132. When member 130 projects a minimum height above surface 132, positioning apparatus 80 is then placed on mounting surface 204 such that first member 84 of the apparatus rests on mounting surface 204. As seen in FIG. 8, probe 202 attached to indicator 200 is then positioned in contact with reference surface 132 of second member 86. A reference value, comprising the value shown by the indicator display when probe 202 is in contact with surface 132, is then noted.

Figure 9:
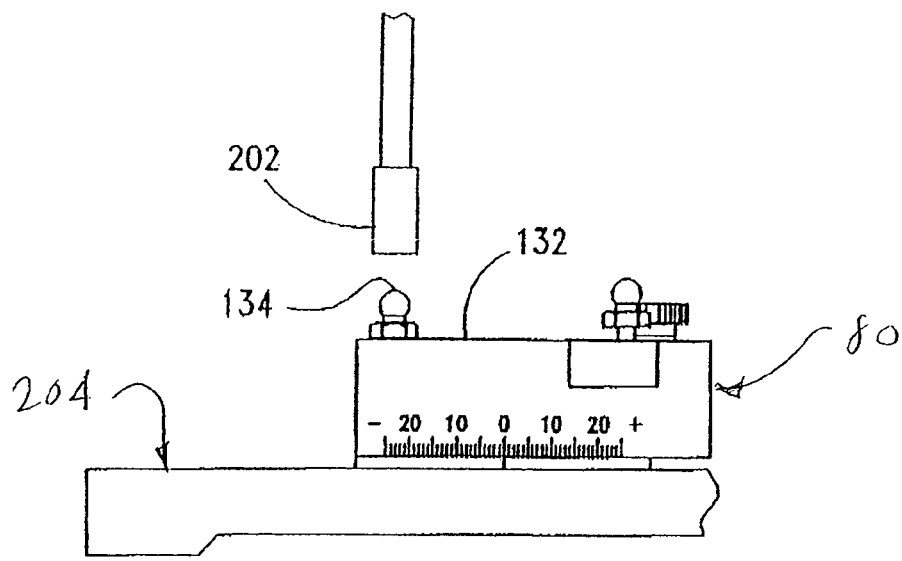
Figure 10:
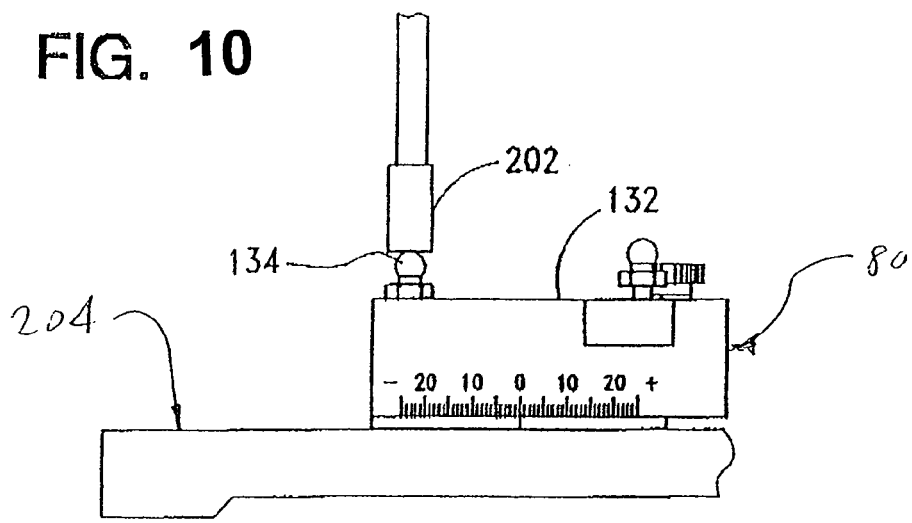
Figure 13:
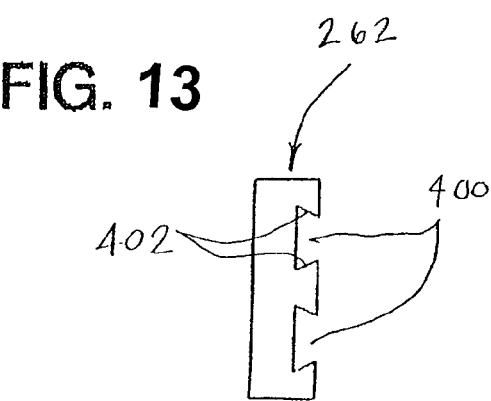
FIG. 13 is an end view of an engagement member of the present invention.
Figure 14:
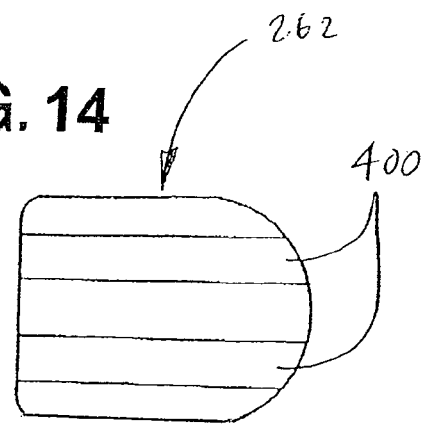
FIG. 14 is a bottom view of an engagement member of FIG. 13.

Next, as seen in FIGS. 9 and 10, probe 202 is positioned so as to rest atop rounded-head portion 134 of locating member 130. Then, with probe 202 in contact with rounded-head portion 134 of locating member 130, locating member 130 is positioned with respect to second member surface 132 to correspondingly position probe 202 such that the difference between the value shown by a display of indicator 200 and the reference value corresponds a fourth coordinate of the set of coordinates.

The above procedure may be repeated for positioning adjustment member 122 with respect to reference surface 120 of third member 88 in correspondence with a third coordinate value of the set of coordinates, and for positioning other adjustment member 118 (if any) with respect to reference surface 120 of third member 88 in correspondence with a fifth coordinate value of the set of coordinates.

When second member 86, third member 88, adjustment members 118, 122 and locating member 130 have all been positioned in correspondence with respective ones of the coordinate values, mounting member 66 is then positioned atop adjustment members 118, 122 and locating member 130 such that rounded head portions 126, 124 of adjustment member screws 118, 122 are received in cavities 72, 128 of mounting member 66. Similarly, rounded head portion 134 of locating member 130 is received in cavity 136 of mounting member 66.

A method for positioning a model of a maxillary dental arch within a dental articulator to simulate the position of the dental arch in the skull of a patient will now be discussed.

Figure 15:
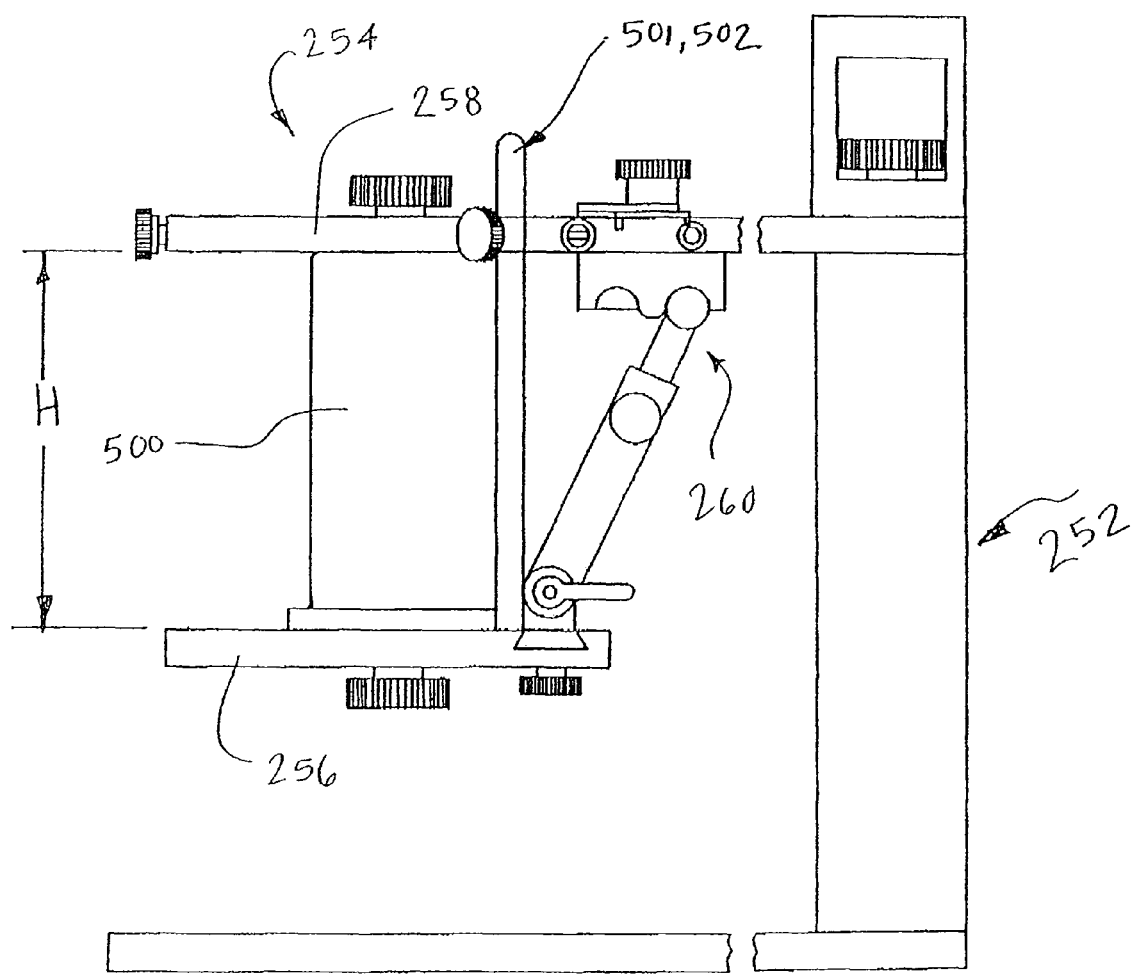
FIG. 15 is a side view of a dental articulator assembly for receiving therein the positioning apparatus of FIG. 2.

FIG. 15 shows a dental articulator assembly, generally designated 250, designed to accurately reproduce the various movements of a patient's lower jaw with respect to the temporomandibular joint, thus allowing for the replication of the patient's teeth in the form of a dental cast. An articulator assembly of the type described below is disclosed in Alpern et al., U.S. Pat. No. 5,320,528, which is incorporated by reference herein.

Articulator assembly 250 includes a base portion 252 and an articulator portion 254 detachably mounted to base portion 252 in a first orientation, articulator portion 254 including a first support member 256, a second support member 258, and joint means, generally designated 260, for simulating the mandibular condylar joint and for mounting first support member 256 to second support member 258 such that first support member 256 is adjustably spaced apart from second support member 258. The '528 patent describes in detail the structure of the articulator means used for adjusting the separation distance between second support member 258 and first support member 256, and for securing the first and second support members in a desired orientation with respect to each other.

Prior to positioning a dental arch model in articulator portion 254, a separation distance H between first support member 256 and second support member 258 is set to a pre-determined value. In one embodiment, a spacer block 500 is positioned to abut second support member 258. first support member 256 is then positioned and secured so as to abut a lower surface of spacer block 500, and rear adjustment rods 501, 502 are locked in position, in a manner described in Alpern et al. '528, to maintain a minimum spacing of H between the first and second support members. Spacer block 500 is formed with at least one dimension corresponding to a desired pre-determined spacing H to be maintained between first and second support members 256, 258.

Referring to FIG. 15, when pre-determined spacing H between first support member 256 and second support member 258 has been provided, first support member 256 is urged downward to enable removal of spacer block 500 from articulator portion 254. As described in detail in Alpern et al. '528, coil springs (not shown) connecting first and second support members 256 and 258, respectively, and rear lateral adjustment rods 501, 502 act to maintain the spatial relationship between first support member 256 and second support member 258 during manipulation of first support member 256.

Figure 16:
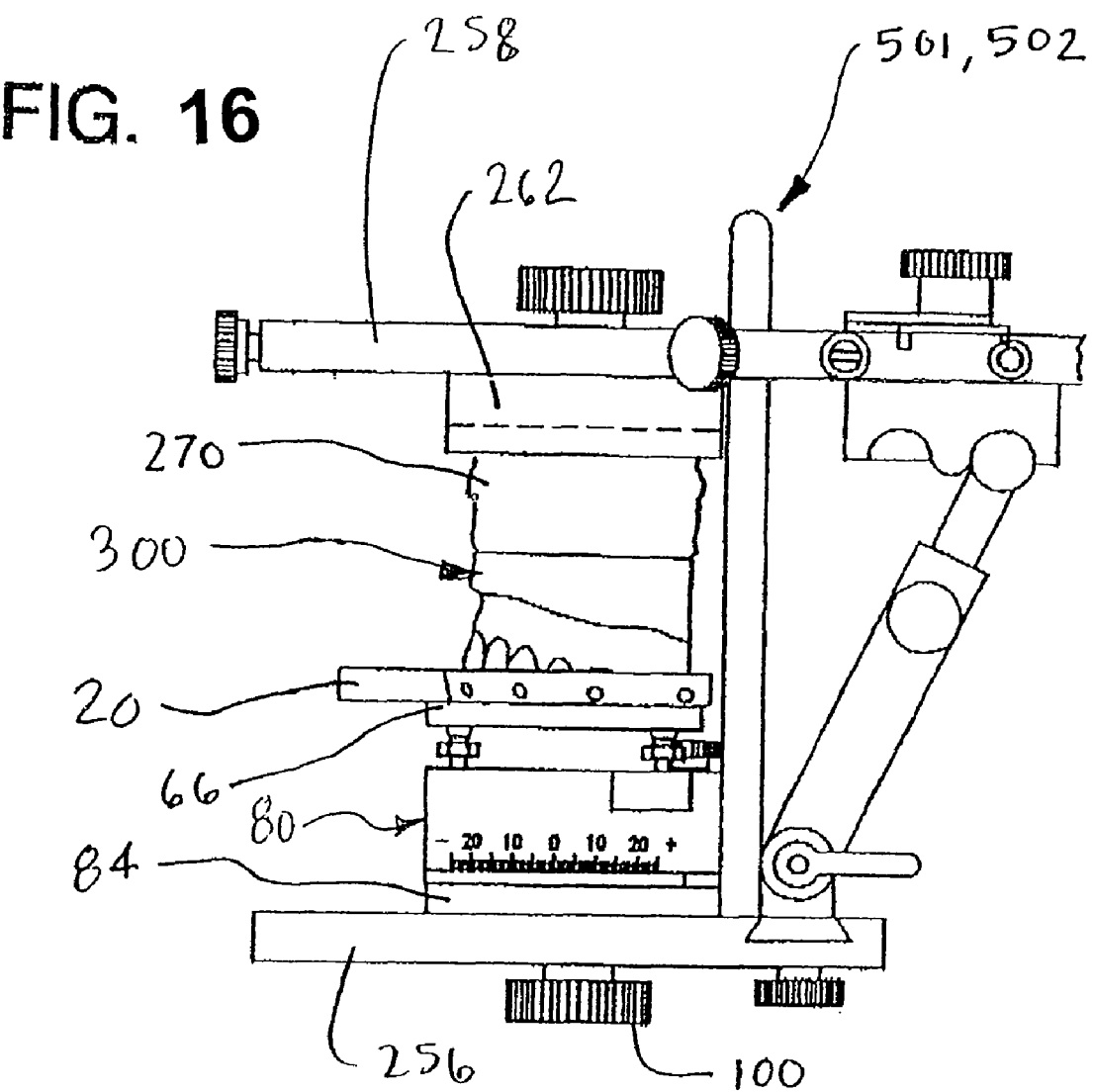
FIG. 16 is a side view of the positioning apparatus of FIG. 2 mounted in the dental articulator of FIG. 15 showing securement of a maxillary arch model to the articulator.

Referring to FIG. 16, the positioning and securing of a dental arch model within articulator assembly 250 will now be discussed. The method for positioning the model of a dental arch within the articulator employs positioning device 20 previously described. Prior to securing positioning apparatus 20 to first support member 256, the positioning apparatus is configured using a set of pre-determined coordinate values as previously described to impart an orientation to mounting member 66 corresponding to the orientation of the maxillary occlusal plane of a patient.

In the embodiment described, the dental arch model is a model of the maxillary arch of the patient. Maxillary arch model 300 is placed in tray 20 with the "teeth side" of the model resting in receptacle 40 and oriented such that the right side of the model (i.e., the portion of the model representing the right side of the patient's dental arch) is proximate the hole in third member labeled "R". A portion of arch model 300 is configured to produce an interference fit with wall 46 of tray 20 when arch model 300 is positioned within tray 20, thereby retaining arch model 300 within tray 20.

To secure the dental arch model to the articulator, first member 84 of positioning apparatus 80 is secured to first support member 256 of articulator portion 254 using a mounting knob 100 as described in the '528 patent, thereby securing positioning apparatus 80 to first support member 256. Mounting member 66 is then positioned atop uppermost surfaces of locating member 130 and adjustment members 118, 122 as previously described. Maxillary matrix tray 20, including maxillary arch model 300 received in tray receptacle 40, is then secured atop mounting member 66. Tray 20 may be secured atop mounting member 66 by, for example, application of an adhesive.

Referring to FIGS. 13-16, an engagement member 262 is provided for attachment to second support member 258 of articulator portion 254. Engagement member 262 has a pair of slots 400 extending along a length of the member with undercuts 402 formed along either side of the slot. After positioning tray 20 and maxillary arch model 300 atop mounting member 66, engagement member 262 is secured to second support member 258 using, for example, a mounting knob 100 as described in the '528 patent.

Figure 17:
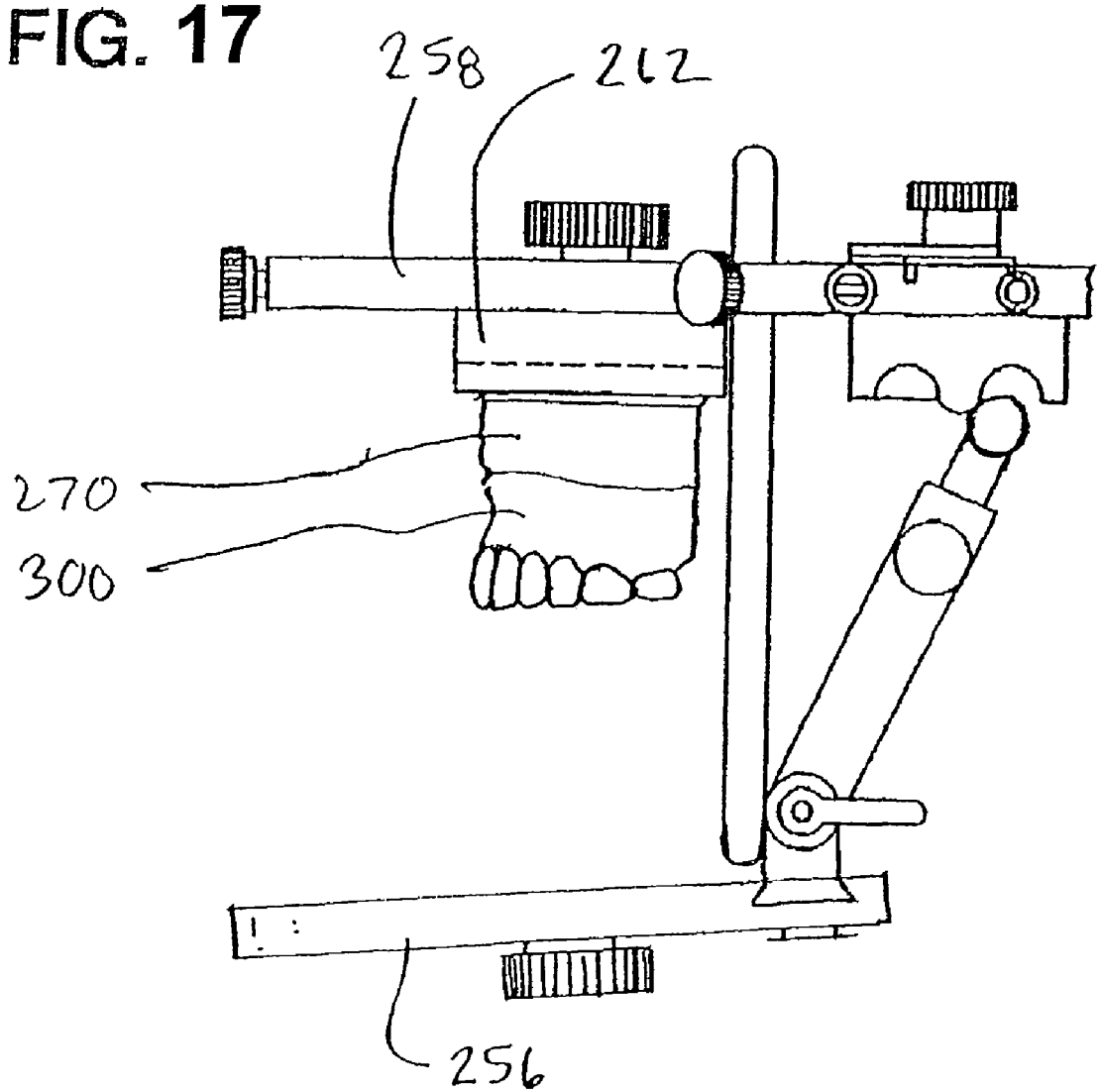
FIG. 17 is a side view of the articulator of FIG. 2 showing the articulator opened to permit removal of the positioning apparatus.

An adhesive material, generally designated 270, is provided which has both a flowable state and a non-flowable state within a temperature range centered about room temperature (approximately 75 degrees F.). Adhesive material 270 in its flowable state is then applied to an uppermost surface of maxillary arch model 300 and to a lowermost surface of engagement member 262 in such a manner and quantity that adhesive 270 connects engagement member 262 with maxillary arch model 300. As a result, when adhesive 270 hardens to a non-flowable state, the adhesive and maxillary arch model to which it adheres will be secured to engagement member 262 (FIG. 17).

Upon securing maxillary arch model 300 to articulator portion 254, it may be desired to secure a model of the mandibular arch of the patient to the articulator portion as well. The following procedure may be used to secure a model of the mandibular arch to articulator portion 254.

Figure 18:
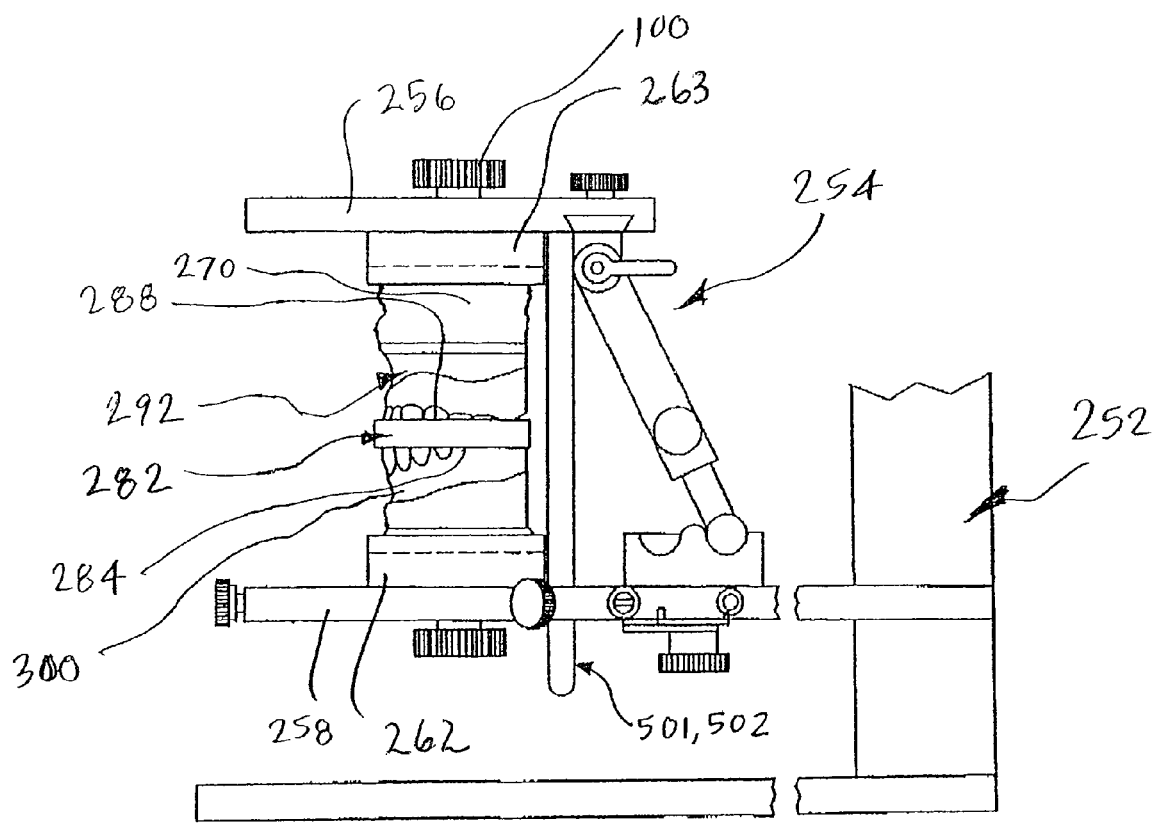
FIG. 18 is a side view of the articulator of FIG. 15 showing both the maxillary and mandibular arch models mounted in the articulator in a first orientation.

Referring to FIG. 18, to secure a mandibular arch model (generally designated 292) to articulator portion 254, a second engagement member 263 is provided similar in configuration to engagement member 262 previously described. In addition, an impression 282 of the patient's bite registration is provided having a first portion 284 which conforms to a bite surface of maxillary arch model 300 and a second portion 288 which conforms to a bite surface of mandibular arch model 292. First support member 256 is then urged downward to enable removal of positioning apparatus 80. Articulator portion 254 is then detached from base portion 252 and inverted as shown in FIG. 18. Articulator portion 254 is then mounted to base portion 252 in the inverted orientation. Second engagement member 263 is then secured to first support member 256 using, for example, a mounting knob 100, as described in the '528 patent. First portion 284 of bite registration impression 282 is then positioned along the bite surface of maxillary arch model 300 that conforms to first portion 286 of impression 282.

Next, a surface of mandibular arch model 292 is positioned along the portion 288 of bite registration impression 282 that conforms to this surface of mandibular arch model 292. Adhesive material 270 in the flowable state is then applied to a lowermost surface of second engagement member 263 and to an uppermost surface of mandibular arch model 292 in such a manner and quantity that adhesive 270 connects second engagement member 263 with mandibular arch model 292. As a result, when adhesive 270 hardens to a non-flowable state, the adhesive and mandibular arch model to which it adheres will be secured to second engagement member 262.

Figure 19:
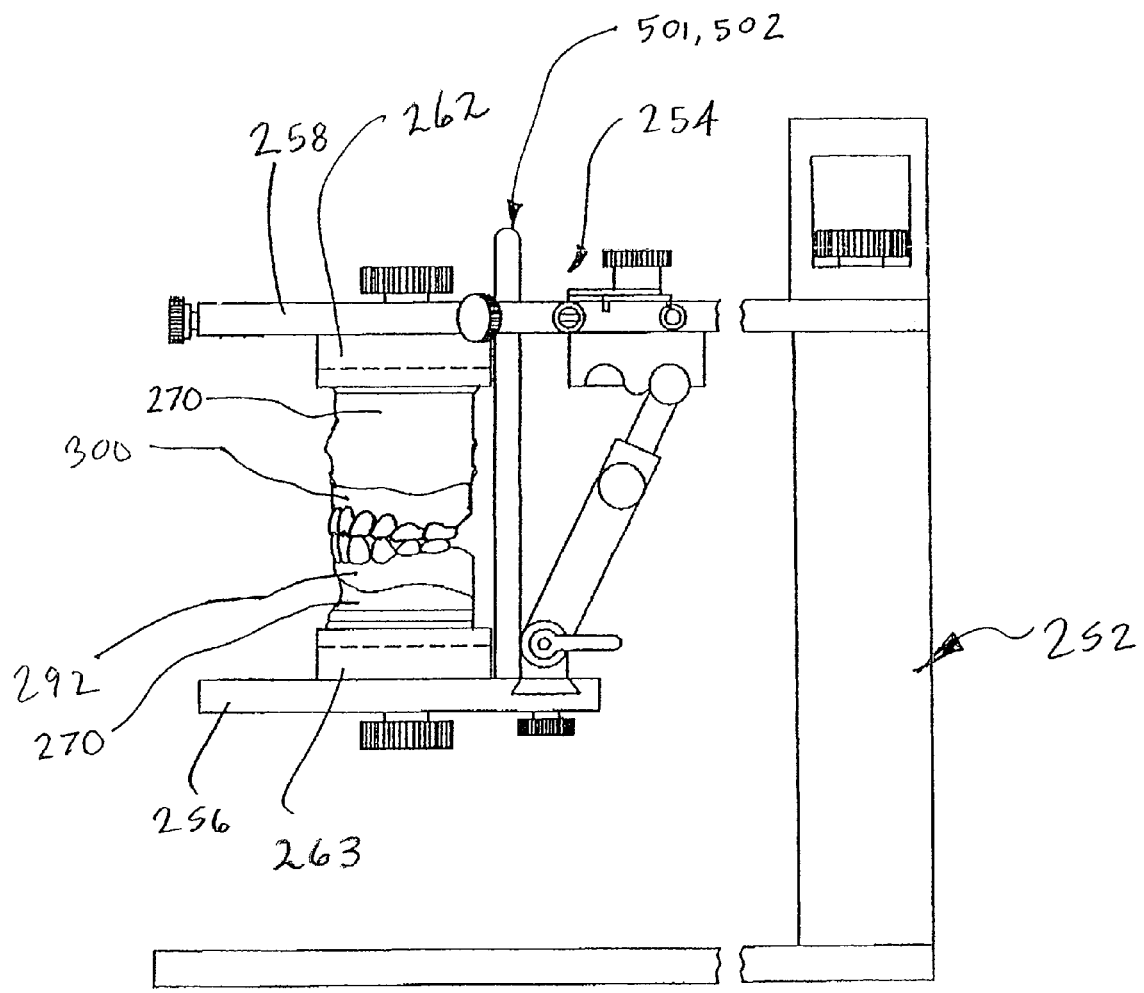
FIG. 19 is a side view of the articulator of FIG. 15 showing both the maxillary and mandibular arch models mounted in the articulator in a second orientation.

Referring to FIG. 19, articulator portion 254 is then detached from base portion 252 and inverted again, thus returning articulator portion 254 to its original orientation. Portion 254 is then secured on base portion 252 in this original orientation. In the resulting arrangement, maxillary arch model 300 is suspended above mandibular arch model 292 with both of arch models 292, 300 secured in articulator portion 254 so as to simulate the bite structure of the patient.

It should be understood that the preceding is merely a detailed description of various embodiments of this invention and that numerous changes to the disclosed embodiments can be made in accordance with the disclosure herein without departing from the spirit or scope of the invention. The preceding description, therefore, is not meant to limit the scope of the invention. Rather, the scope of the invention is to be determined only by the appended claims and their equivalents.

The invention claimed is:

1. A positioning apparatus for simulating a position of a dental arch within an articulator, comprising:

a first member that may be disposed on a support member of a dental articulator;

a second member wherein the first member defines one of a projection and a groove and the second member defines the other of the projection and the groove such that the projection extends into the groove and the first and second member are movable relative to each other along the groove and along a first axis and wherein the second member defines a slot positioned along an arc path;

a third member positioned within the slot and capable of sliding within the slot along the arc path, wherein the arc path of the slot is positioned spaced apart from a second axis and wherein the second axis is positioned perpendicular to the first axis; and a locating member associated with the second member wherein the locating member comprises an end, and wherein the end is adjustable relative to a surface of the second member, first and second adjustment members associated with the third member, wherein each of the first and second adjustment members comprises an end, and wherein each end is adjustable relative to a surface of the third member, a mounting member wherein one side of the mounting member defines first, second and third cavities adapted to receive the end of the locating member and the first and second adjustment members, and wherein the mounting member comprises another side adapted to receive a maxillary tray, and a maxillary tray comprising three radio opaque members positioned wherein the first, second and third radio opaque members are positionable to respectively overlie the first, second and third cavities of the mounting member.

2. The positioning apparatus of claim 1 wherein the first, second and third members are constructed of metal.

3. The positioning apparatus of claim 1 wherein the projection comprises a dovetail-shaped tongue.

4. The positioning apparatus of claim 3 wherein the groove is constructed of a shape and a size to receive the dovetail-shaped tongue.

5. The positioning apparatus of claim 1 further comprises a locking member which secures the first and second member.

6. The positioning apparatus of claim 5 wherein the locking member comprises a set screw.

7. The positioning apparatus of claim 1 wherein the first member comprises one of a reference indicator mark and a series of coordinate indicator marks and the second member comprises the other one of the reference indicator and the series of coordinate indicator marks.

8. The positioning apparatus of claim 7 wherein the reference indicator mark and the series of coordinate indicator marks are positioned adjacent to one another.

9. The positioning apparatus of claim 1 wherein the first and second adjustment members comprise a screw, each screw having an end positionable with respect to a surface of the third member and wherein the screw engages a bore defined in the third member.

10. The positioning apparatus of claim 1 wherein the locating member comprises a screw having an end positionable with respect to a surface of the second member and wherein the screw engages a bore defined in the second member.

11. The positioning apparatus of claim 10 wherein the locating member is positioned within a second axis.

12. The positioning apparatus of claim 11 wherein the second axis is positioned generally perpendicular to the first axis.

13. The positioning apparatus of claim 12 wherein the second axis is spaced apart from the arc path and contains a center of the arc path.

14. The positioning apparatus of claim 1 wherein the third member comprises an arcuate shape and is adapted to be received by the slot.

15. The positioning apparatus of claim 14 further comprising a locking member to lock together the second and third members.

16. The positioning apparatus of claim 15 wherein the locking member comprises a set screw.

17. The positioning apparatus of claim 7 wherein the second member comprises one of a second reference indicator mark and a second series of coordinate indicator marks and the third member comprises the other of the second reference indicator mark and the second series of coordinate indicator marks.

18. The positioning apparatus of claim 17 wherein the other reference indicator and the second series coordinate indicator marks are positioned adjacent to one another.

19. The positioning apparatus of claim 17 wherein the position of the first reference mark with respect to the first series of coordinate indicator marks, the position of the second reference mark with respect to the second series of coordinate indicator marks, the position of the locating member, and the positions of the first and second adjustment members are derived from measurements of a patient's head in combination with radiographic data.

20. The positioning apparatus of claim 19 wherein the radiographic data is determined from anterior, lateral, and submental X-ray views of the patient's head, wherein the patient's teeth are engaged in the maxillary tray.

* * * * *